United States Patent [19]

Baxter, Jr.

[11] 3,944,791

[45] Mar. 16, 1976

[54] PLATELET COUNT CORRECTION CIRCUIT

[75] Inventor: Robert Baxter, Jr., Stratford, Conn.

[73] Assignee: General Science Corporation, Bridgeport, Conn.

[22] Filed: July 10, 1974

[21] Appl. No.: 486,817

[52] U.S. Cl..... 235/92 PC; 235/92 PL; 235/92 DN; 235/92 R; 324/71 CP
[51] Int. Cl.² .......................................... H03K 21/34
[58] Field of Search ....... 235/92 PC, 92 PL, 92 CV, 235/92 EC, 92 LG; 324/71 CP

[56] References Cited
UNITED STATES PATENTS

| | | | |
|---|---|---|---|
| 3,764,781 | 10/1973 | Kreithen et al. | 235/92 PL |
| 3,790,910 | 2/1974 | McCormack | 235/92 PL |
| 3,827,045 | 7/1974 | Markus | 235/92 CV |
| 3,864,551 | 2/1975 | Oefinger | 235/92 PC |

Primary Examiner—Gareth D. Shaw
Assistant Examiner—John P. Vandenburg
Attorney, Agent, or Firm—Weingarten, Maxham & Schurgin

[57] ABSTRACT

Circuitry for the correction of error occasioned during the counting of platelets in a hematology system. A coincidence corrected platelet count is provided as an input to a rate counter which provides a plurality of output signals representative of different percentages of the input count. A read-only memory is employed to store data representing correction factors for different hematocrit values. Gating circuitry is enabled by output signals from the read-only memory representing a selected hematocrit correction factor, the enabled gate circuits providing pulses representative of selected percentages of the input count and which are combined to provide an output pulse train which is the corrected platelet count.

4 Claims, 3 Drawing Figures

PLATELET COUNT CORRECTION CIRCUIT

FIELD OF THE INVENTION

This invention relates to particle counting systems and more particularly to circuitry for correction of platelet count error.

BACKGROUND OF THE INVENTION

Systems are known for counting blood cells or other particles suspended in a liquid, a preferred system being shown in U.S. Pat. No. Re. 27,902 assigned to the assignee of the present invention. In such a system, electrical pulses are provided in response to the passage of particles through a metering aperture of a transducer or conductivity cell which is disposed within a fluid path and which has electrodes on respective opposite sides of the aperture. The impedance of the fluid path is materially altered by the presence of a particle within the aperture, resulting in production of electrical pulses corresponding to the number of particles passing through the aperture and which pulses are electronically counted to provide an output indication of particle count. A known volume of particle-containing liquid is usually metered by appropriate means to provide a particle count for a known volume of liquid.

Such systems are often employed for counting platelets within a suitably diluted platelet sample. The platelet count is subject to coincidence error which arises by reason of the coincident or nearly coincident passage of more than one particle through the metering aperture of the conductivity cell and which is sensed as a single particle, resulting in the number of measured particles being lower than the actual particle count for a given quantity of sample liquid. The platelet count is also dependent upon measured hematocrit value. Correction charts are usually employed to provide a corrected platelet count. It would be preferable however to employ automated means to directly provide a corrected platelet count to thereby overcome the time and susceptibility to error occasioned by the usual manual use of correction charts.

SUMMARY OF THE INVENTION

Briefly, the invention provides a correction circuit for use in a platelet counting system in which a coincidence corrected platelet count is automatically and continuously corrected to provide a corrected count. Input pulses representing a coincidence corrected platelet count are applied to an electronic rate counter or scaler which provides a plurality of output signals representative of different percentages of the input pulse count. These output signals are applied via suitable gating circuitry to respective gate circuits which are selectively enabled by output signals from a read-only memory. The read-only memory has stored therein data representing hematocrit correction factors for a range of hematocrit values. A hematocrit reading is entered as an input to the read-only memory by suitable input switches or other means, the memory providing a plurality of output signals representing the hematocrit correction factor and which signals are operative to enable selected ones of the gate circuits. The enabled gate circuits provide pulses representative of selected percentages of an input count and these pulses are combined in an output gate to provide an output pulse train which represents corrected platelet count.

DESCRIPTION OF THE DRAWINGS

The invention will be more fully unerstood from the following detailed description taken in conjunction with the accompanying drawings, in which.

DETAILED DESCRIPTION OF THE INVENTION

Figure 1:
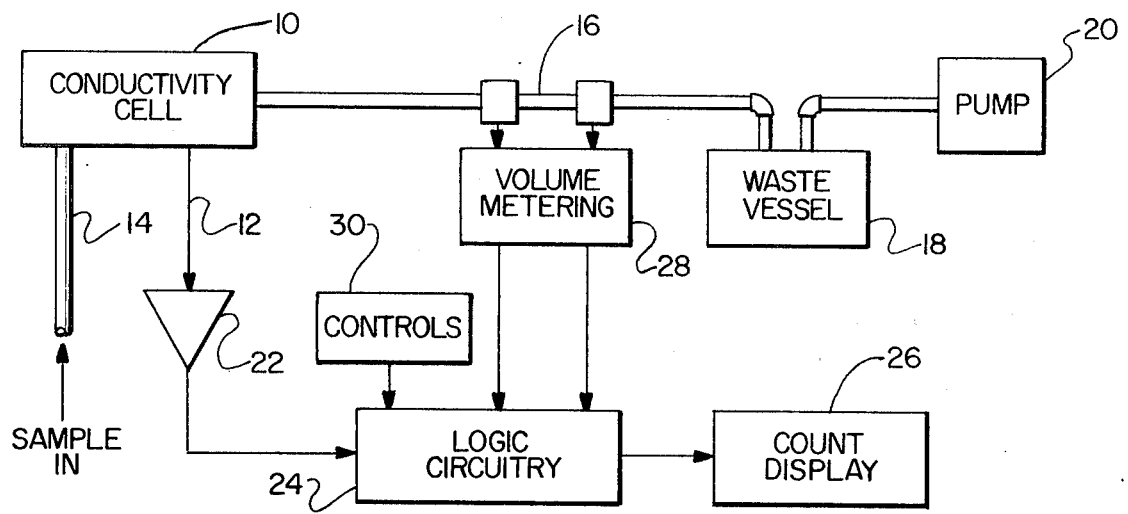
FIG. 1 is a schematic representation of a particle counting system in which the invention is useful.

A particle counting system in which the invention is useful is shown diagrammatically in FIG. 1 and which itself is the subject of U.S. Pat. No. Re. 27,902. This system includes a conductivity cell or transducer 10 having a metering aperture and electrodes therein for providing electrical pulses on output line 12 corresponding and in response to particles passing through the aperture thereof. Particle-containing liquid is drawn from a sample container into cell 10 via an input tube 14 and exits through a tube 16 which terminates in a waste vessel 18 which is also coupled to pump 20. Pump 20 provides a negative pressure for drawing sample liquid through cell 10 for analysis during a counting run. The output pulses from cell 10 are applied to an amplifier 22, the output of which is coupled to logic circuitry 24 which processes the received pulses to provide an output signal to a count dislay 26 which visually indicates the particle count for a given quantity of sample liquid. The sample quantity being analyzed is determined by volume metering means 28 which senses a known quantity of sample liquid flowing through tube 16 and provides electrical start and stop signals to logic circuitry 24 to define a counting interval within which a particle count is accumulated for display. Appropriate controls 30 are coupled to logic circuitry 24 for operation thereof.

Figure 2:
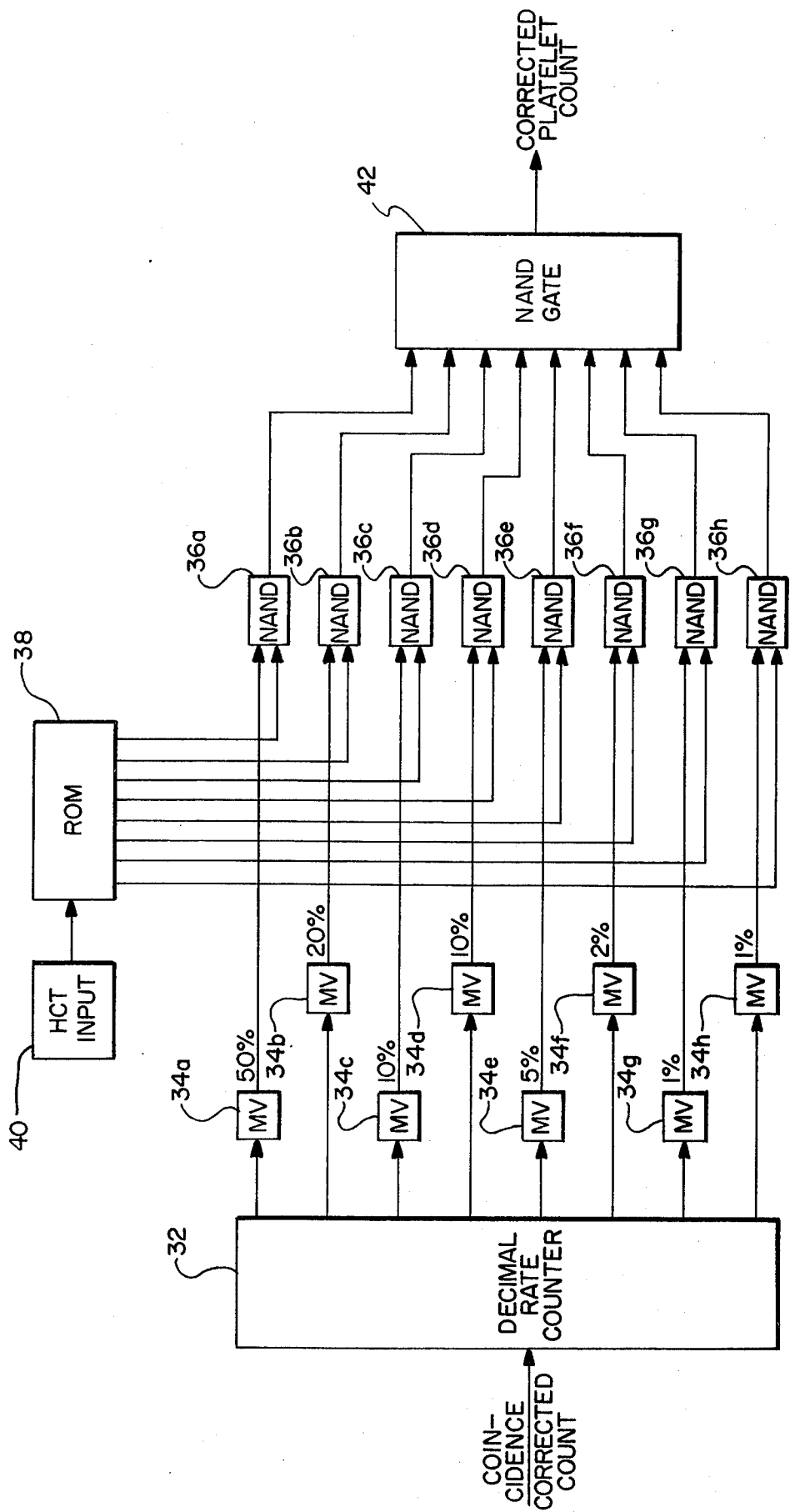
FIG. 2 is a block diagram representation of a platelet correction circuit according to the invention.

The system shown in FIG. 1 can be employed for counting platelets suspended within a blood sample, and, according to the invention, a platelet count is obtained which is corrected for coincidence error occasioned by the simultaneous passage of two or more particles through the metering aperture of the conductivity cell 10 and also corrected in accordance with a corresponding hematocrit reading. The novel circuitry of the invention is shown in FIG. 2 and inclues a decimal rate counter or scaler 32 receiving input pulses representative of a coincidence corrected platelet count. The coincidence corrected count is provided by the logic circuitry 24 of the system of FIG. 1 and particularly by circuitry to be desribed hereinbelow. Such circuitry for providing a coincidence corrected count is preferably of the type shown in copending application Ser. No. 447,530, filed Mar. 1, 1974, now U.S. Pat. No. 3,864,55, and assigned to the assignee of this invention.

The counter 32 has a plurality of outputs coupled to respective multivibrators 34a–34h and the outputs of which, in turn, are applied to respective NAND gates 36a–36h. An enabling input for each of the NAND gates 36a–36h is provided by a respective output from a read-only memory 38, the input of which is coupled to a hematocrit input source. Memory 38 has stored therein data representing correction factors for a range of hematocrit values. The hematocrit correction factor is equal to $1 - HCT/75$ and this correction factor decreases for increasing values of hematocrit. The output code from read-only memory 38 representing the correction factors selects the gates 36a–36h which are to be enabled to provide the intended percentage of the input count. The outputs of NAND gates 36a–36h are applied to respective inputs of an output gate 42, typically a NAND gate, and the output of which provides the corrected platelet count. The circuit of FIG. 2 is typically implemented in integrated circuit form. Counter 32 is typically constructed of integrated circuit decade counters such as Texas Instruments type 7490. The read-only memory 38 is typically a semiconductor memory programmed in accordance with the correction factors needed for particular input hematocrit values. The hematocrit input source 40 is typically a binary coded switch which provides a coded representation of hematocrit for each manually selected value.

The output signals from counter 32 are representative of selected different percentages of the count applied as an input thereto. The output signals from counter 32 are applied to respective multivibrators 34a–34h which provide corresponding output pulses for subsequent processing. In the illusrated embodiment, the outputs of respective multivibrators 34a–34h represent the respective percentages 50, 20, 10, 10, 5, 2, 1 and 1, of the input count to counter 32. The corrected platelet count is a predetermined percentage of the coincidence corrected input count for selected hematocrit values, and by operation of the invention, read-only memory 38 provides an output code representative of the hematocrit correction factor operative to enable selected ones of gates 36a–36h corresponding to the percentage outputs of counter 32 which when combined will provide the percentage value intended to yield the corrected output count.

Figure 3:
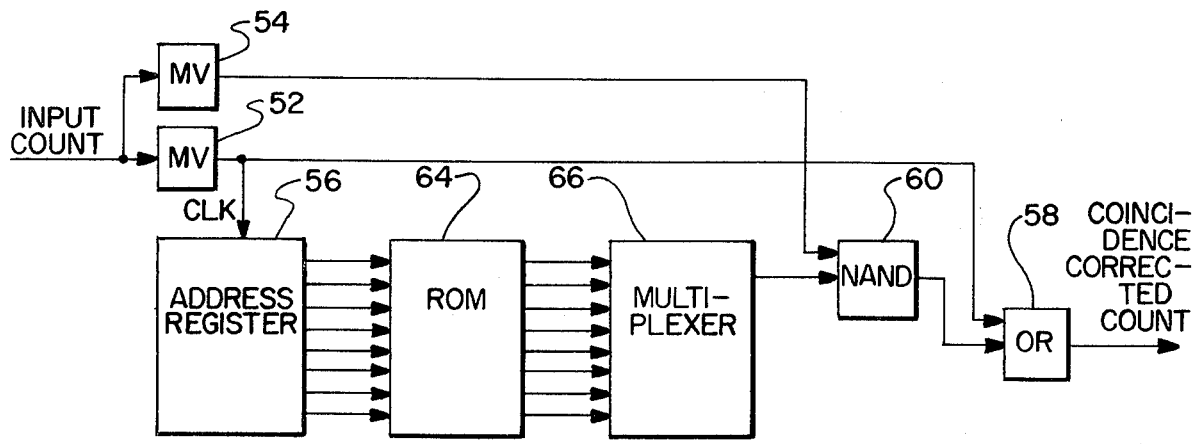
FIG. 3 is a block diagram representation of a coincidence correction circuit useful to provide input pulses to the invention.

The coincidence corrected platelet count pulses provided as an input to the circuitry of FIG. 2 are provided in preferred embodiment by the circuitry shown in FIG. 3 and which is itself the subject of the aforesaid copending application. Referring to FIG. 3, pulses representative of a measured platelet count are applied to first and second multivibrators 52 and 54. Multivibrator 52 provides output pulses as a clock signal to an address register 56 and also provides its output pulses as one input of OR gate 58, the output of which gate is the corrected count. The output pulses from multivibrator 54 are applied as one input to NAND gate 60, the outputs of which are applied to respective inputs of OR gate 58. Address register 56 has its output lines coupled to the inputs of a read-only memory 64, the output of which is coupled to a multiplexer 56 which provides an output signal to gate 60. The multivibrators 52 and 54 typically are one shot multivibrators, multivibrator 52 being triggered on the trailing edge of an input pulse while multivibrator 54 is triggered on leading edge of the input pulse. As a result, a predetermined time delay is provided between the respective output pulses from the multivibrators sufficient to permit signal processing for providing correction data.

The address register 56 provides an output code corresponding to the number of clock pulses applied thereto and which code addresses a read-only memory 64 which has stored therein data representative of the coincidence points of a correction chart at which additional pulses are to be added to a measured count. At the addresses of the stored data, memory 64 provides an output code to multiplexer 66 which produces an output signal to gate 60 to cause an additional pulse to be added to the measured count for correction.

In operation, pulses provided by transducer or conductivity cell 10 (FIG. 1) and of a number representative of measured platelet count are applied to multivibrator 52 which provides corresponding output pulses to OR gate 58 which, in turn, provides output pulses for subsequent processing and display. The input pulses are also applied to multivibrator 54 which provides corresponding pulses to an iput of NAND gate 60. Address register 56 is operative in response to the clock pulses provided by multivibrator 52, and which in turn is representative of the input pulses to provide a parallel output code to sequentially address memory 64 in accordance with successive values of the received particle count. At selected addresses of the data stored in memory 64, the memory provides an output code to multiplexer 66 which in turn provides an output signal to gate 60. The enabled gate 60, upon receipt of a signal from multiplexer 66 and multivibrator 54, provides an output pulse to OR gate 58 which provides a correction pulse for addition to the then count. Read-only memory 64 is typically a semiconductor memory programmed in accordance with the corrections needed for a particular aperture size an dilution ratio of the sample liquid.

It will be appreciated that the invention can be implemented in a variety of forms to suit specific operating and constructional requirements without departing from the spirit and true scope of the invention. Accordingly, it is not intended to limit the invention by what has been particularly shown and described except as indicated in the appended claims.

What is claimed is:

1. In a platelet counting system including a transducer having an aperture through which platelet-containing liquid is caused to flow, means for generating electrical pulses in response to platelets passing through said aperture, and circuitry for providing correction for the coincident passage of multiple particles through said aperture, circuitry for providing output indication of corrected platelet count comprising:
    counter means operative in response to coincidence corrected platelet count to provide a plurality of output signals representative of selected percentages of said coincidence corrected count;
    signal representation means for providing signal representations of hematocrit values;
    correction factor means operative in response to said signal representations to provide corresponding output signals representative of hematocrit correction values; and
    gate means selectively enabled by said output signals from said correction factor means and operative to transmit and combine selected ones of said counter means output signals
    to provide an output pulse train representative of corrected platelet count.

2. The invention according to claim 1 wherein said signal representation means includes:
    manually actuable input means for providing coded signal representations of hematocrit values; and
    wherein said correction factor means includes:
    a memory means having stored therein data representing hematocrit correction factors for different hematocrit values.

3. The invention according to claim 2 wherein said gate means includes a plurality of gates each operative to receive a respective one of said counter means output signals, said gates being selectively enabled in accordance with the output signals from said memory means representing hematocrit correction factor for a selected value of hematocrit.

4. In a platelet counting system including a transducer having an aperture through which platelet-containing liquid is caused to flow, means for generating electrical pulses in response to platelets passing through said aperture, and circuitry for providing correction for the coincident passage of multiple particles through said aperture, circuitry for providing output indication of corrected platelet count comprising:

counter means operative in response to coincident corrected platelet count to provide a plurality of output signals each representative of a selected different percentage of said coincidence corrected platelet count;

memory means having data representing hematocrit correction factors for a range of different hematocrit values and operative in response to an input code to provide a selected plurality of enabling signals;

input means for providing said input code to said memory means and representing a selected hematocrit value;

a plurality of gate means each enabled by a respective one of said memory means enable signals and each receiving a respective one of said counter means output signals; and output gate means receiving the output signals from the enabled ones of said plurality of gate means an operative to provide an output signal representative of a selected percentage of the coincidence corrected platelet count and being the corrected platelet count.

* * * * *